Figure 1:
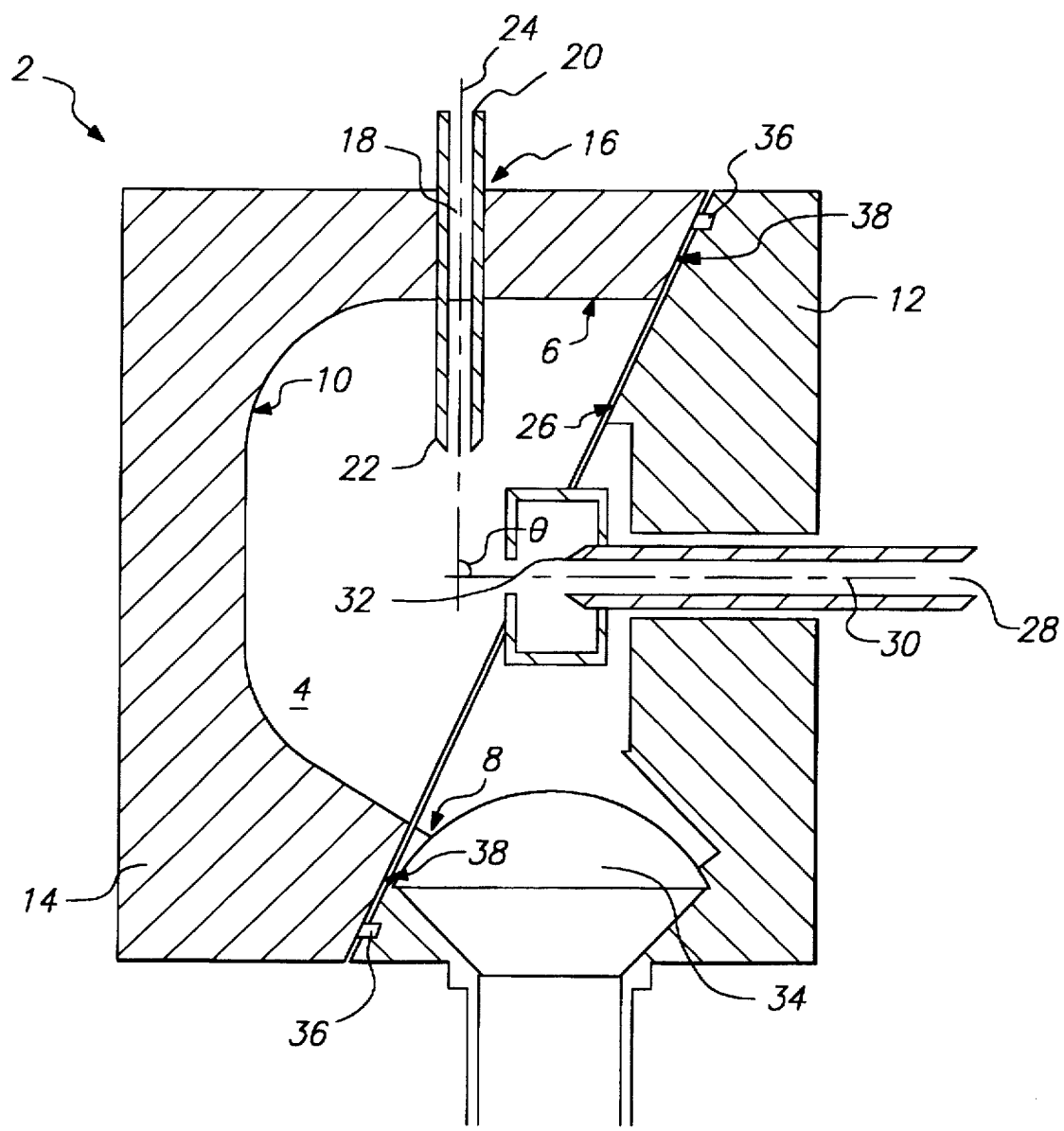

United States Patent [19]
Gourley et al.

[11] Patent Number: 5,753,910
[45] Date of Patent: May 19, 1998

[54] ANGLED CHAMBER SEAL FOR ATMOSPHERIC PRESSURE IONIZATION MASS SPECTROMETRY

[75] Inventors: Darrell L. Gourley, San Francisco; Eugene M. Wong, Campbell; James L. Bertsch; Robert G. Nordman, both of Palo Alto, all of Calif.

[73] Assignee: Hewlett-Packard Company, Palo Alto, Calif.

[21] Appl. No.: 679,481

[22] Filed: Jul. 12, 1996

[51] Int. Cl.$^6$ .............................. B01D 59/44; H01J 49/00
[52] U.S. Cl. .............................. 250/288; 250/281
[58] Field of Search .............................. 250/281, 282, 250/288

[56] References Cited

U.S. PATENT DOCUMENTS

| | | | |
|---|---|---|---|
| 4,647,772 | 3/1987 | Lewis et al. | 250/282 |
| 4,851,700 | 7/1989 | Goodley | 250/281 |
| 5,412,208 | 5/1995 | Covey et al. | 250/282 |
| 5,495,108 | 2/1996 | Apffel, Jr. et al. | 250/288 |
| 5,559,326 | 9/1996 | Goodley et al. | 250/281 |

FOREIGN PATENT DOCUMENTS

WO 95/24259   9/1995   WIPO.

*Primary Examiner*—Bruce Anderson

[57] ABSTRACT

An atmospheric pressure ionization source is provided which includes an ionization chamber that is formed from the combination of an angled chamber body and a correspondingly angled chamber seal. The ionization chamber is used for electrospray or atmospheric pressure chemical ionization of a liquid sample to provide ionized molecules. The ionized molecules can be passed to an associated analytical device that is capable of detecting and measuring the mass-to-charge ratio and/or the mass and charge of the molecules. A mass spectrometer which includes the present atmospheric pressure ionization source is also provided, as well as a liquid chromatography/mass spectrometry (LC/MS) analysis system which includes an LC/MS interface comprising the present atmospheric pressure ionization source.

26 Claims, 4 Drawing Sheets

ANGLED CHAMBER SEAL FOR ATMOSPHERIC PRESSURE IONIZATION MASS SPECTROMETRY

TECHNICAL FIELD

The invention relates generally to components of a mass spectrometer. More particularly, the invention relates to an atmospheric pressure ionization source having an angled ionization chamber seal, mass spectrometer devices which include the atmospheric pressure ionization source, and liquid chromatography/mass spectrometer (LC/MS) devices which use the atmospheric pressure ionization source in an LC/MS interface.

BACKGROUND OF THE INVENTION

Mass spectrometry is used for quantitative elemental analysis, identification of chemical structures and the determination of molecular weight and/or composition of mixtures. Mass spectrometry can be used to ascertain the molecular weights of molecules or the identity of components of a sample based on the detection of a fragmentation pattern of ions produced when the material is ionized.

Mass spectrometry involves the formation of ions from analyte molecules, the separation of the various ions according to their mass-to-charge ratio (m/z), and the subsequent generation of a mass spectrum obtained from the separated ions as a result of their having passed through an electric field, a magnetic field or a combination thereof.

The combination of mass spectrometry with liquid chromatography or capillary electrophoresis separation techniques provides a powerful analytical approach to identifying molecular species in a liquid sample. Such systems have the ability to separate solutions containing mixtures of organic or inorganic molecules into liquid fraction effluents containing discrete compounds. In order to analyze the effluents with a mass spectrometer which operates in a high vacuum system, the liquid effluent is generally prepared for ionization and analysis using atmospheric pressure ionization sources such as electrospray and Atmospheric Pressure Chemical Ionization (APCI) sources. When interfaced to mass spectrometers, electrospray and APCI ionization sources can be used to produce ions from continuously flowing liquid samples to provide on-line detection for liquid chromatography separation systems.

Electrospray and APCI ion sources produce ionized molecules from a liquid sample at or near atmospheric pressure within an ion source chamber, and deliver the ionized molecules into vacuum where they are accelerated and focused into a mass analyzer. Electrospray ionization provides charged droplets which, upon evaporation, produce ions directly from liquid to gas phase. APCI ionization involves more steps, wherein the liquid sample is initially evaporated to convert analytes from liquid to gas phase. Gas phase ions are produced by chemical ionization charge exchange with solvent ions produced in a corona discharge region located within the atmospheric pressure source chamber. Each ionization technique is suited to complementary classes of molecular species.

Electrospray ionization is generally more concentration dependent, wherein higher analyte concentration equates to better performance. Electrospray ionization works well in the analysis of moderate and highly polar molecules, and is particularly well suited for analysis of large biological molecules and pharmaceuticals, such as those that ionize in solution and exhibit multiple charging. Electrospray ionization also performs well for small, fairly polar molecules.

APCI ionization is much less dependent upon analyte concentration, and performs quite well with smaller nonpolar or moderately polar molecules. With APCI ionization, higher flow rates generally enhance performance.

Both electrospray ionization (ESI) and APCI ion sources need to be cleaned and regularly maintained between ionization operations. Sample analyte residues that are left over from previous operations can cause significant spectral and/or chemical background noise due to resampling during subsequent operations, as well as provide a source of contamination. Thus, the internal components of such ion sources, including nebulizer tips, inner chamber walls, electrodes, end plates, sample passageways and exhaust/drain lines, need to be carefully cleaned on a regular basis. In practice then, atmospheric ion sources must be disassembled to provide access to the internal components. However, even in a disassembled condition, the internal chamber components of such sources are not easily accessible for complete cleaning and maintenance. This is particularly so with conventional ion sources that generally have a box-like configuration.

SUMMARY OF THE INVENTION

The invention provides an ion source capable of conducting atmospheric pressure ionization, whether electrospray or atmospheric pressure chemical ionization (APCI), with a liquid sample to provide ionized molecules. The source can be used to interface a liquid separation system, for example, a liquid chromatography system, with a mass analyzer device in order to detect separated analyte components in the liquid eluant. The ion source can also be used to interface other means of providing a liquid sample with a mass analyzer device, such as but not limited to, flow injectors, syringe pumps, infusion pumps or the like. The ion source comprises an ionization chamber that is formed from the combination of an angled chamber body and a correspondingly angled chamber seal. The angled configuration of the chamber seal and body provides for greatly enhanced user accessibility to the internal components of the ionization chamber when the chamber is opened or disassembled.

The novel angled configuration of the chamber seal represents a substantial departure from conventional square chamber seals which rely on sliding doors to provide access to chamber components. Further, the angled configuration allows the positioning of the chamber components to be optimized relative to each other within the ionization chamber to provide for more efficient analyte enrichment and a related reduction in chemical and/or spectral background in an apparatus employing the ion source. Reducing the chemical and/or spectral background results in increased signal-to-noise ratios, thereby providing greater sensitivity capabilities in associated analytical devices.

In one aspect of the invention, the angled configuration of the chamber seal and body allows a sample introduction means disposed in the ionization chamber seal to be arranged substantially opposite to an exhaust or drain port disposed in the chamber body such that it remains fixed relative to the instrument mainframe when the ionization chamber is disassembled by removing the seal. This arrangement avoids the use of sliding liquid seals, such as in a ionization chamber system which includes a drain or exhaust port that is disposed within the chamber seal. The fixed exhaust or drain port facilitates the ease with which the ionization chamber can be opened or disassembled for routine user maintenance or adjustment of the ionization chamber components. Positioning of the sample introduction means opposite the drain in the ionization chamber allows for smoother aerodynamic flow out of the chamber which decreases resampling problems caused by backflow and/or eddy currents within the chamber. Further, when electrospray ionization is being conducted, such positioning removes aerosol and liquid rapidly from the ionization chamber to prevent problems associated with condensation, dripping and/or pooling of sample within the chamber. When APCI ionization is being conducted, the capability of directing the hot sample vapor directly into an exhaust port allows heat to be rapidly removed from the chamber, reducing the need to cool the chamber.

In another aspect of the invention, the angled configuration of the chamber seal and body allows for the substantially orthogonal arrangement between a sample introduction means disposed in the chamber seal and a sampling exit or passageway disposed in the chamber body. When the ionization chamber is opened or disassembled, both the sample introduction means and the entrance to the sampling exit are readily accessible for cleaning and maintenance. Orthogonal ion sampling can be carried out using the present ion sources, whereby a more efficient enrichment of the sample analyte is attained by spraying charged sample ions past the sampling exit to direct solvent vapor and solvated droplets away from the entrance to an associated mass analyzer.

In a further aspect of the invention, a mass spectrometer is provided having an atmospheric pressure ionization source with an ionization chamber that is formed from the combination of an angled chamber body and a correspondingly angled chamber seal. The mass spectrometer can be used to mass analyze a wide variety of analytes and can be operated under numerous conditions. By arranging the sample introduction means and associated charging sources on the chamber seal, the ion source can be readily switched between electrospray and APCI ionization modes of operation by merely interchanging chamber seals that have been configured for each type of ionization technique. Further, effluent from liquid separation systems can be ionized in the ionization chamber for analysis in the mass spectrometer under high flow rate conditions, such as effluent flow rates of greater than about 1 mL/min that are typical with High Performance Liquid Chromatography (HPLC) systems, or at particularly low flow rate conditions, such as effluent flow rates of less than about 1 μL/min (e.g., microspray or nanospray) that are typical with capillary electrophoresis (CE) and capillary electrochromatography (CEC) separation systems.

In yet a further aspect of the invention, a liquid chromatography/mass spectrometry (LC/MS) system is provided having an LC/MS interface comprising an atmospheric pressure ionization source with an ionization chamber that is formed from the combination of an angled chamber body and a correspondingly angled chamber seal.

BRIEF DESCRIPTION OF THE FIGURES

FIG. 1 is a cross-sectional representation of an atmospheric pressure ion source having an angled chamber seal.

FIG. 2 is a cross-sectional representation of an atmospheric pressure ion source configured for use in electrospray ionization.

FIG. 3 is a cross-sectional representation of an atmospheric pressure ion source configured for use in APCI ionization.

FIG. 4 is a pictorial representation of a liquid chromatography/mass spectrometry (LC/MS) analysis system showing a cross-sectional representation of an LC/MS interface that comprises an atmospheric pressure ion source having an angled chamber seal.

DETAILED DESCRIPTION OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "a sample analyte" includes two or more analytes, reference to "an attachment means" includes two or more such means, and the like.

In this specification and in the claims which follow, reference will be made to a number of terms which shall be defined to have the following meanings:

The term "passageway" as used herein includes any form of ion guide whatsoever. Thus, the term encompasses a passageway that is of such short length relative to its opening diameter that it may be referred to as an orifice. Other suitable ion guides such as capillaries are generally known to those of skill in the art. Thus a number of different passageway configurations can be interchangeably used herein and specifically described configurations are not intended to be limiting.

In one embodiment of the invention, an ion source is provided for producing ionized molecules from a liquid sample at or near atmospheric pressure. The ion source can also be operated at pressures above or below atmospheric pressure, such as in those certain applications where it is desirable to ionize the sample under increased or decreased pressure. Referring to FIG. 1, an ion source 2 is depicted which comprises an ionization chamber, generally indicated at 4, having a top portion 6, a bottom portion 8 and a back portion 10. The ionization chamber 4 is formed by the operative combination of a chamber body 12 and a chamber seal 14. The chamber seal 14 provides the top and back portions, indicated at 6 and 10 respectively, of the ionization chamber. The chamber seal is comprised of suitable materials such as stainless steel, aluminum or aluminum alloys. A sample introduction means, generally indicated at 16, is disposed within the chamber seal and arranged such that it extends through the top portion 6 of the ionization chamber 4. The sample introduction means 16 is used to conduct a liquid sample from a suitable source; for example, a liquid chromatograph column, a flow injector system, a syringe pump, an infusion pump, or the like, and deliver the sample into the ionization chamber 4 in a suitable form. Particularly, the sample introduction means comprises a first passageway 18 having an upstream terminus 20 for communication with the sample source, and a downstream terminus 22 which communicates with the ionization chamber 4. The first passageway extends along a central axis 24 of the sample introduction means 16 and discharges atomized sample, e.g., an aerosolized or nebulized spray, from the downstream terminus, 22, into the ionization chamber.

The chamber body 12 provides the bottom portion 8, and an exit interface portion 26 of the ionization chamber 4. The chamber body is comprised of suitable materials such as stainless steel, aluminum or aluminum alloys. A second passageway 28 is disposed within the chamber body and arranged such that a central axis 30 thereof is in transverse relation with the central axis 24 of the sample introduction means. An orientation angle θ is thereby formed between the major axis of the atomized sample exiting from the first passageway and the central axis of the second passageway. The second passageway 28 has an inlet 32 which is capable of accepting charged molecules generated within the ionization chamber 4 for communication thereof to an associated analytical device. The chamber body 12 also includes an outlet means 34 which extends through the bottom portion 8 of the ionization chamber 4 and serves as an exhaust or drain port for the chamber.

In operation, the ion source 2 is assembled by affixing the chamber seal 14 to the chamber body 12 using associated attachment means, such as a spring clip or other biasing fastener, thereby defining the ionization chamber 4. Optionally, a gasket 36 can be used to provide a gas- and liquid-tight seal, wherein an O-ring or other suitable sealing means is interposed between a slanted shoulder 38 of the chamber seal 14 and a correspondingly slanted surface of the exit interface portion 26 provided by the chamber body 12. The gasket material is selected so as to be chemically resistant and able to withstand the elevated operating temperatures associated with the ion source. One particularly suitable gasket material is formed from polytetrafluoroethylene, however a number of other suitably resistant gasket materials can also be used.

The shoulder 38, and the surface of the exit interface portion 26 are identically angled relative to a vertical axis such that when the ionization chamber 4 is opened by detaching the seal from the chamber body, the internal components of the ionization chamber, including the downstream terminus 22 of the sample introduction means 16, the entrance to the second passageway 28, the outlet means 34 and the interior walls of the ionization chamber are readily accessible for inspection, cleaning, maintenance and/or replacement. When the ionization chamber is opened, the outlet means and any associated drain lines or conduits remain associated with the chamber body 12. This feature allows for rapid assembly and disassembly of the ionization chamber without the need of connecting or disconnecting exhaust or drain conduits. The novel angled configuration of the chamber seal and body allows for greatly enhanced user access to all of the key components of the ionization chamber. Such access exceeds that of conventional ionization chamber designs which employ a sliding door configuration for access to the internal components of the chamber.

Referring still to FIG. 1, the sample introduction means 16 is arranged in the ionization chamber 4 such that the downstream terminus 22 of the first passageway 20 is in opposing relation to the outlet means 34. The outlet means can be arranged such that when the ionization chamber is assembled, a central axis of the outlet means 34 is substantially in axial alignment with the downstream terminus 22 of the sample introduction means. In one embodiment, the outlet means 34 is substantially 180 degrees opposed to the sample means in the assembled chamber. Alternatively, the outlet means can be arranged to be in facing relation with, but have a central axis that is linearly or angularly offset from, the downstream terminus 22 of the sample introduction means. Each of these configurations allow for rapid and efficient exhaust of sample vapor and liquids from the ionization chamber through the outlet means, providing for the aerodynamic flow of atomized sample through the chamber. The capability to efficiently exhaust the ionization chamber and maintain an aerodynamic flow therethrough avoids problems associated with condensation and/or pooling of sample liquids within the chamber.

When the ion source is used in electrospray ionization, having the outlet means in opposing relation to the sample introduction means removes aerosol and liquid rapidly from the ionization chamber particularly during high flow operations, e.g., liquid flow greater than about 400 μL/min. This helps to eliminate or drastically reduce pooling of the sample which could cause chemical/spectral background noise as the pool evaporates in the hot environment of the ion source. When the ion source is used in APCI ionization, having the outlet means in opposing relation to the sample introduction means allows the hot vapor to be dumped directly into the exhaust vent. The amount of heat retained within the ionization chamber is thereby substantially reduced, avoiding the need to cool the chamber.

The sample introduction means 16 discharges a liquid sample from the downstream terminus 22 into the ionization chamber under conditions suitable to create an aerosol of charged droplets or "electrospray." The liquid sample is generally introduced into the chamber at flow rates of about 1 μL/min to about 5000 μL/min, and preferably at a rate of about 10 μL/min to about 2500 μL/min. When the ionization chamber is used in conjunction with CE or CEC separation systems which provide effluent at very low flow rates, e.g., about 20 nanoliters/min to about 400 nanoliters/min, make-up flows can be used to bring the sample flow rates up to the preferred range for introduction into the chamber. Transport of the electrospray into the second passageway 28 proceeds laterally, wherein charged molecules in the electrospray move in a direction that is transverse to the direction of flow from the sample introduction means. More particularly, the relative orientation angle θ between the major axis of vapor exiting from the first passageway and the central axis of the second passageway is preferably between about 75 and 105 degrees. Although the angle θ can be greater than about 105 degrees, optimal results are obtained when the angle is kept at or near 90 degrees. Accordingly, in one embodiment, transport of the electrospray into the second passageway proceeds in a substantially orthogonal direction, e.g., wherein θ is 90 degrees. Charged electrospray droplets are moved across the ionization chamber 4 between the downstream terminus 22 of the sample introduction means and the inlet 32 of the second passageway by virtue of electrostatic forces established by connecting voltage sources to various components of the ionization chamber.

The ion source 2 can be used in electrospray or APCI ionization operations to produce ionized molecules from a liquid sample. Embodiments of the ion source that are configured for electrospray or APCI share a number of ionization chamber components with each other, particularly those associated with or affixed to the chamber body 12. Thus, the various device configurations depicted herein can be interchangeably adapted for either ionization technique with relatively straightforward modification of the sample introduction means. Further, chamber seals configured for either electrospray or APCI ionization can be interchanged with each other in combination with a single chamber body, allowing for rapid conversion between ionization sources in a single device. If desired, magnetically or electrically coded contacts can be provided on the surface of the chamber body which couples with the slanted shoulder of the chamber seal. The contacts can recognize the ionization configuration (e.g., electrospray or APCI) provided by each different type of chamber seal, and supply suitable operating instructions to an associated analytical device. In addition, optional safety interlocks can also be provided to disconnect high voltage and heat sources from the chamber upon opening or disassembly of the ionization chamber. Particularly, safety interlock switches, such as magnetic contact or position sensors, can be provided on the surface of the chamber body which couples with the slanted shoulder of the chamber seal. These switches can be used to sense opening of the chamber and provide appropriate signals to disconnect high voltage and heat sources from the chamber.

Figure 2:
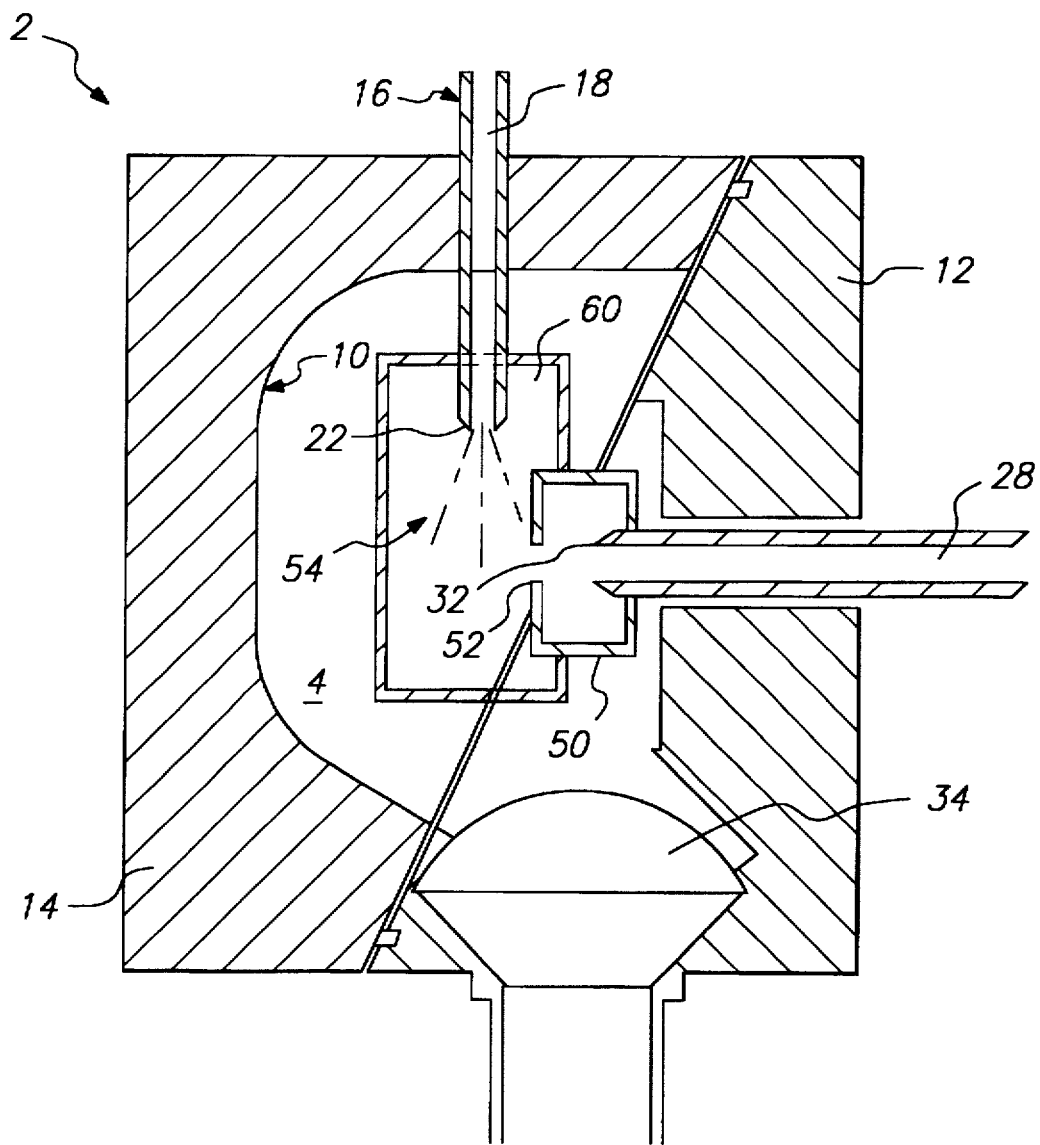

Referring now to FIG. 2, the ion source 2 is configured for use in electrospray ionization of a liquid sample. The second passageway 28 is optionally contained within an electrically conductive housing 50 which has an opening 52 arranged adjacent to the downstream terminus 22 of the first passageway 18 of the sample introduction means 16. A first voltage source is connected to the housing 50, and a second voltage source is connected to the inlet 32 of the second passageway 28, thereby establishing first and second ionization chamber electrodes. The electrospray sample introduction means 16, which generally comprises a nebulizer such as an ultrasonic or pneumatic nebulizer, discharges an aerosol 54 of liquid sample into the ionization chamber 4. As the aerosol 54 emerges from the sample introduction means, analyte molecules contained therein become ionized due to the presence of a strong electrical field established within the ionization chamber 4. In particular, a high electrical potential is established between the first passageway 18 and the first and second ionization chamber electrodes, such as wherein the first passageway is maintained at ground, and the first and second electrodes are maintained at kilovolt settings. Ionized particles are electrostatically attracted into the second passageway 28 by the first and second ionization chamber electrodes.

The electrospray ion sources can be used to generate either positively or negatively charged molecules (ions) depending on the relative charges applied to the electrodes in the ionization chamber. In one particular embodiment, the second voltage source is set at −4.5 kV and the first voltage source at −4 kV which establishes an electrical potential between the inlet 32 of the second passageway 28 and the housing 50. This particular electrical potential helps to focus movement of ions into the second passageway. Furthermore, a flow of an inert drying gas can be established through the opening 52 of the housing 50 in order to remove solvent from the ionized droplets as they pass into the second passageway. Suitable drying gases include nitrogen, carbon dioxide or argon. The drying gas is generally kept at about 25° to 400° C., and is passed across the opening 52 at a rate of about 3 to 15 L/minute.

The sample introduction means 16 can be arranged in a variety of configurations so long as the distance between the high voltage portions of the ionization chamber is sufficient to prevent arcing or electrical discharge. In related electrospray embodiments, the ion source 2 can include additional high voltage sources disposed within the ionization chamber 4 which alter the shape of the electric fields encountered by the aerosol 54. In this manner, generation of ionized analyte molecules in the electrospray can be effectively maximized, and the resulting spray of ionized droplets more tightly focused within the chamber. For example, in the ion source of FIG. 2, the walls of the ionization chamber 4 can optionally be grounded in order to help contain the ionized aerosol and route condensed aerosol to the outlet means 34 for removal from the ionization chamber.

In other electrospray systems, additional chamber electrodes can be provided within the chamber to provide, for example, a third voltage source which can be set at a positive voltage relative to the first voltage source connected to the housing 50. As will be appreciated by those skilled in the art after reading the present specification, the repellant effect provided by the additional voltage source can be optimized to sculpt the electrical field within the ionization chamber, thereby enhancing the ion collection characteristics of the second passageway.

Referring particularly to the embodiment depicted in FIG. 2, the ion source can be configured to include a third voltage source in the form of a full-cylinder, annular electrode 60, which is shown in cut-away view in the figure. The annular electrode 60 encompasses the aerosol 54 exiting from the downstream terminus 22 of the first passageway 18 and aids in establishing a strong electrical field for ionization of the aerosol by virtue of the potential difference between the annular electrode 60 and the downstream terminus 22.

The ion sources of the invention can also be configured for use in APCI ionization of a liquid sample. APCI ionization entails multiple steps wherein the liquid sample is initially nebulized to provide droplets of the mobile phase (solvent) and analyte molecules. The nebulized sample droplets are vaporized using heat to desolvate the droplets. A dry vapor of solvent and analyte molecules is provided which is discharged into the ionization chamber. The solvent molecules are ionized by a corona discharge within the chamber, and the analyte molecules are then chemically ionized by the solvent ions at atmospheric pressure.

Figure 3:
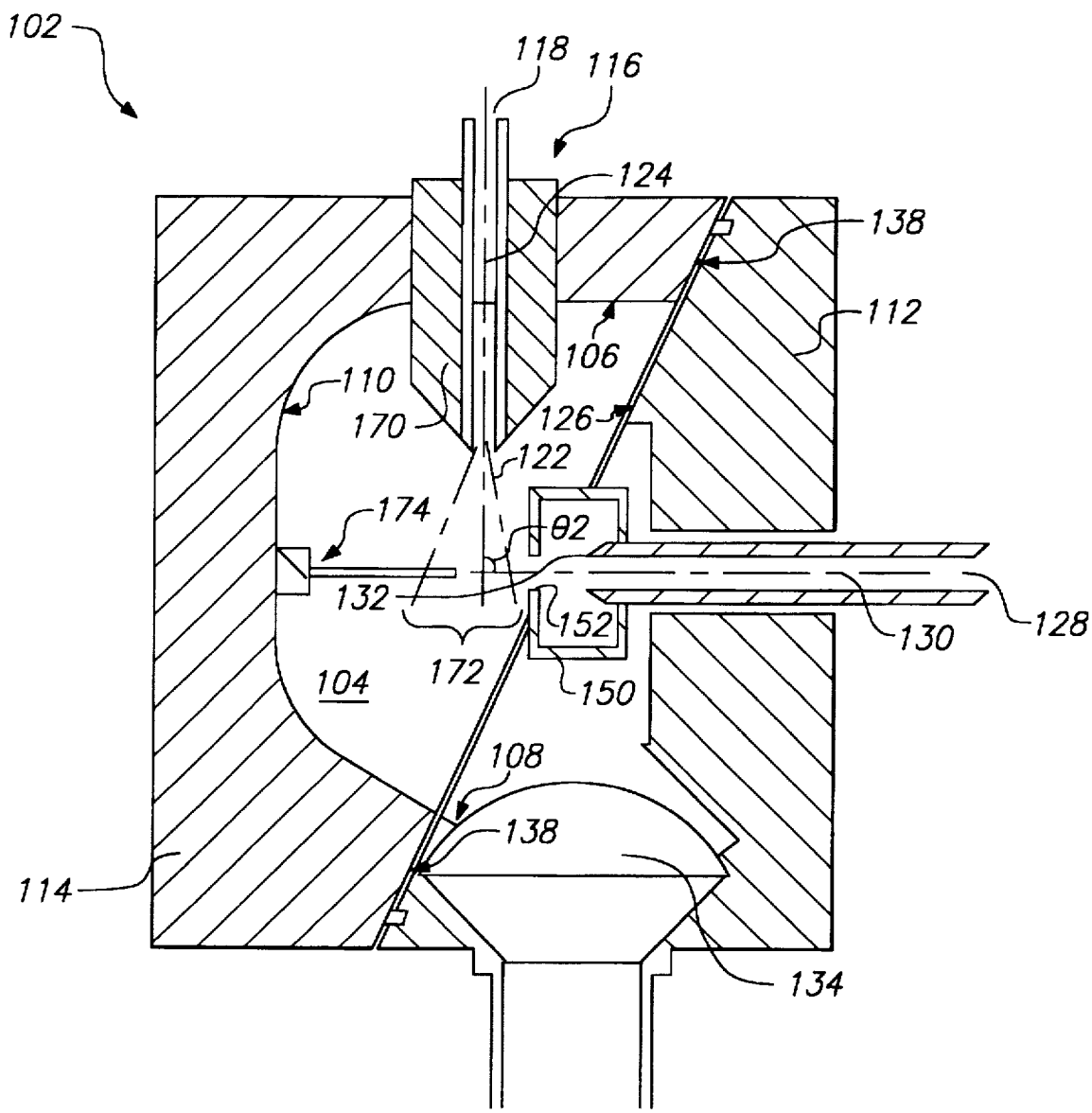

Referring now to FIG. 3, one embodiment of an APCI ion source is generally indicated at 102. The ion source comprises an ionization chamber, 104, having a top portion 106, a bottom portion 108 and a back portion 110. The ionization chamber 104 is formed from the combination of an angled chamber body 112 and a correspondingly angled chamber seal 114. The chamber seal 114 provides the top and back portions, 106 and 110, of the ionization chamber. A sample introduction means, generally indicated at 116, is disposed within the chamber seal and arranged such that it extends through the top portion 106 of the ionization chamber 104. The sample introduction means comprises a vaporization chamber which accepts a nebulized liquid sample containing solvent and sample analyte droplets, and creates a vapor therefrom which is discharged into the ionization chamber. The sample introduction means 116 includes a first passageway 118 formed from an elongated conduit comprised of a suitable material such as glass, ceramic or the like. A closely associated heating element 170 is used to provide controlled heating along the length of the first passageway 118. The temperature of the first passageway can be adjusted relative to the volatility of the solvent such that complete vaporization is achieved without concomitant thermal degradation of the analyte. The first passageway further includes a downstream terminus 122 from which vaporized solvent and analyte droplets exit into an intervening space or gap 172 within the ionization chamber 104. A point charge voltage source 174, such as a corona needle or other suitable source, is disposed on the chamber seal 114 and positioned on the back portion 110 of the ionization chamber so as to optimally contact and induce charge transfer among the molecules present in the gap 172. The electrical discharge provided by the point charge voltage source 174 causes ionization of the solvent molecules which subsequently chemically ionize the analyte to provide sample ions.

The chamber body 112 provides the bottom portion 108 of the ionization chamber as well as an exit interface portion 126. A second passageway 128, having an inlet 132, is provided in the chamber body. The second passageway passes through the exit interface portion and is arranged such that a central axis 130 thereof is in transverse relation with a central axis 124 of the sample introduction means. The second passageway can optionally be contained within an electrically conductive housing 150 which has an opening 152 arranged adjacent to the downstream terminus 122 of the first passageway. A first voltage source is connected to the housing 150, and a second, stronger relative voltage source is connected to the inlet 132 of the second passageway 128, thereby providing electrostatic attractive forces which cause ionized analyte molecules contained within the gap 172 to enter into the second passageway.

Transport of the ionized analyte molecules into the second passageway 128 proceeds laterally, wherein charged molecules move in a direction that is transverse to the direction of flow from the sample introduction means. Thus, the relative orientation angle θ2 between the major axis of vapor exiting from the first passageway and the central axis of the second passageway is generally kept at about 75 to 105 degrees. In one embodiment, transport proceeds in a substantially orthogonal direction, e.g., wherein θ2 is 90 degrees.

In operation, the point charge voltage source 174 can be run in either a positive (+) or negative (−) mode, typically at about 1 to 5 kV, and the walls of the ionization chamber can be maintained at ground. The first and second voltage sources are oppositely charged relative to the point charge voltage source, such as wherein the first voltage source is set at about −3.5 kV and the second voltage source at about −4 kV.

The chamber body 112 also comprises an outlet means 134 which extends through the bottom portion 108 of the ionization chamber and serves as an exhaust for the heated vapor. The ion source 102 is assembled by affixing the chamber seal 114 to the chamber body 112 to define the APCI ionization chamber. Particularly, a shoulder 138 of the chamber seal 114, and a corresponding surface of the exit interface portion 126 are identically angled relative to a vertical axis such that when the ionization chamber 104 is opened or disassembled by detaching the chamber seal from the chamber body, each of the internal components of the ionization chamber, including the sample introduction means 116, the point charge voltage source 174, the second passageway 128, the outlet means 134, the surface of the housing 150 and the interior walls of the ionization chamber are readily accessible for inspection, cleaning, maintenance and/or replacement.

The electrospray and APCI ionization chambers of the invention provide the capability of performing atmospheric pressure ionization in conjunction with separation techniques such as liquid chromatography and High Performance Liquid Chromatography (HPLC) which are conducted at high sample flow rates. The chambers can also perform atmospheric pressure ionization in conjunction with separation systems operating at very low flow rates, e.g., microspray or nanospray effluents obtained from capillary electrophoresis (CE) or capillary electrochromatography (CEC) separation systems. The operating characteristics of the above separation systems are well known. Essentially, a liquid sample being analyzed is separated into discrete constituent parts which elute from the separation system at different times. The eluted sample constituents, and the solvent (mobile phase) in which they are dissolved, are introduced into the atmospheric pressure ion source wherein desolvated, charged analyte molecules are generated and separated from the comparatively larger volumes of vaporized column effluent. The desolvated molecules are then directed to an associated analytical device.

In particular, ionized sample molecules generated within the electrospray and APCI ionization chambers of the invention can be analyzed using an associated analytical instrument that is capable of detecting and measuring the mass-to-charge ratio of the molecules, such as a mass spectrometer or an equivalent instrument. Thus, the second passageway will generally comprise a capillary, a heated capillary or any other suitable ion guide having a downstream terminus that is in fluid communication with a mass analyzer. The mass analyzer is maintained at high vacuum such that the ionized molecules are accelerated along the second passageway and pass into the entrance of the mass analyzer. Suitable mass analyzers include quadrupole or other multi-pole mass filters, ion trap detectors, magnetic or electric sector detectors, time-of-flight or ion cyclotron resonance mass analyzers, as well as tandem arrangements such as MS/MS devices.

Figure 4:
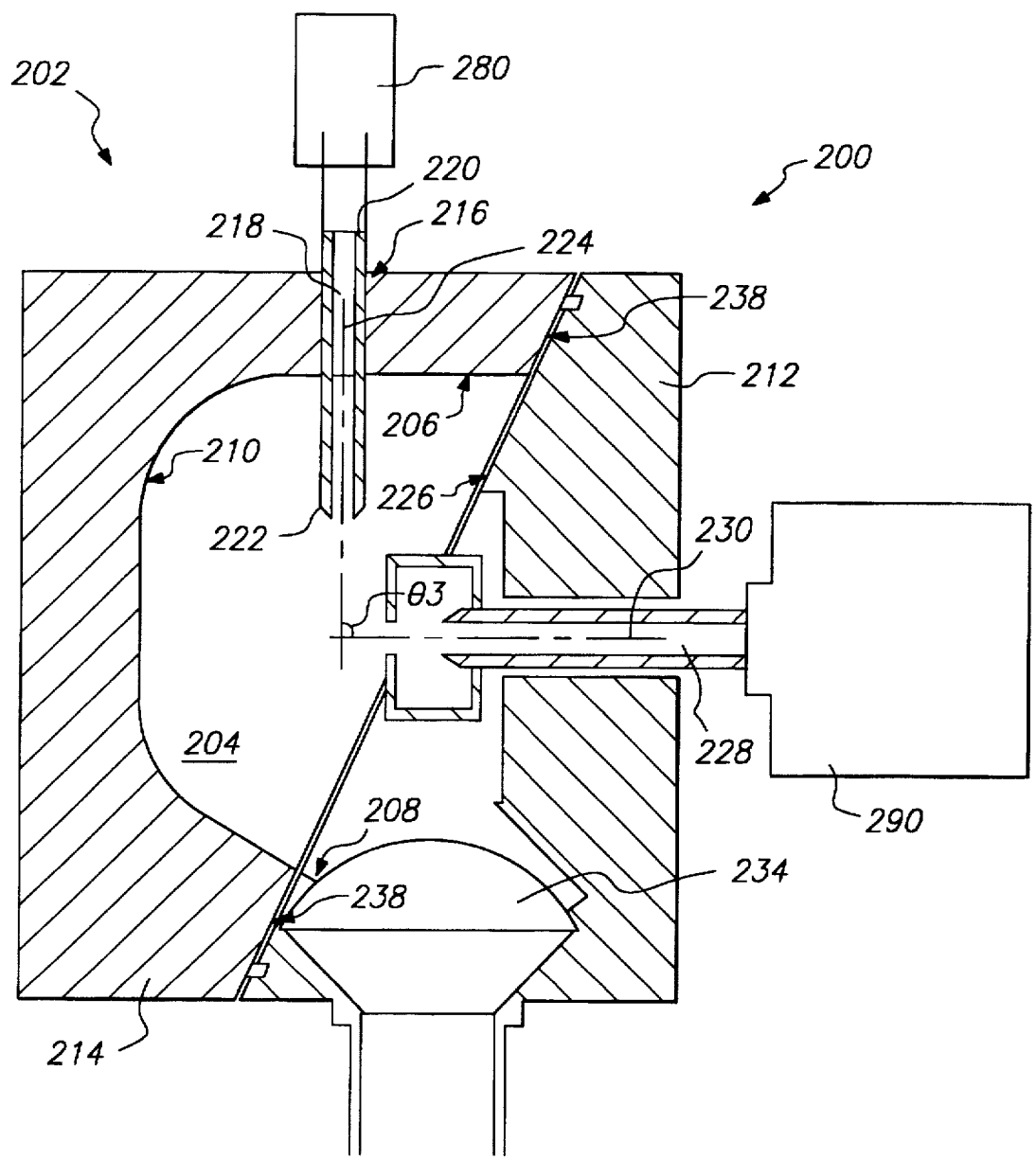

Referring now to FIG. 4, a liquid chromatography/mass spectrometry (LC/MS) system is generally indicated at 200. The LC/MS system includes a liquid chromatography system 280, a mass spectrometer 290 and an LC/MS interface which comprises an atmospheric pressure ionization source, generally indicated at 202, including an ionization chamber 204 configured according to the invention. The ionization chamber has a top portion 206, a bottom portion 208, a back portion 210, and is formed from the combination of an angled chamber body 212 and an angled chamber seal 214 that are identically angled relative to a vertical axis.

The chamber seal 214 provides the top and back portions, 206 and 210, of the ionization chamber. A sample introduction means, generally indicated at 216, is disposed within chamber seal and arranged such that it extends through the top portion 206 of the ionization chamber 204. The sample introduction means 216 comprises a first passageway 218, having an upstream terminus 220 which communicates with the liquid chromatography system 280, and a downstream terminus 222 which communicates with the ionization chamber. The first passageway extends along a central axis 224 of the sample introduction means 216 and discharges atomized sample from the liquid chromatography system into the ionization chamber.

The chamber body 212 provides the bottom portion 208 of the ionization chamber as well as a mass spectrometer interface portion 226. A second passageway 228 is disposed within the chamber body and passes through the interface portion 226 to communicate with the mass spectrometer 290. The second passageway is arranged such that a central axis 230 thereof is in transverse relation with the central axis 224 of the sample introduction means.

The liquid chromatography system 280 separates component analytes of a sample from each other, which sample analytes then emerge from the system in liquid fraction effluents. The effluents are communicated into the ionization chamber 204 via the sample introduction means, whereby the component analytes are ionized to provide an aerosol of charged molecules within the chamber. Transport of the charged analyte molecules into the second passageway 228 generally proceeds laterally, wherein charged molecules move in a direction that is transverse to the direction of flow from the sample introduction means. The charged molecules are transported into the second passageway by the influence of electrostatic attractive forces provided at or near the entrance of the passageway as described above. The relative orientation angle θ3 between the major axis of aerosol exiting from the first passageway and the central axis of the second passageway is generally kept at about 75 to 105 degrees. In one embodiment, transport proceeds in a substantially orthogonal direction, e.g., wherein θ3 is 90 degrees. In this manner, the charged analyte molecules are passed to the mass spectrometer 290 from the second passageway. The mass spectrometer is capable of providing a mass spectrum to permit reliable identification and quantification of the sample analytes separated by the liquid chromatography system 280.

The chamber body 212 also comprises an outlet means 234 which extends through the bottom portion 208 of the ionization chamber and serves as an exhaust or drain port for the chamber. The ion source 202 is assembled by affixing the chamber seal 214 to the chamber body 212 to define the ionization chamber 204. Particularly, a shoulder 238 of the chamber seal 214, and a corresponding surface of the mass spectrometer interface portion 226 are identically angled relative to a vertical axis such that when the ionization chamber 204 is opened or disassembled by detaching the chamber seal from the chamber body, each of the internal components of the ionization chamber are readily accessible for inspection, cleaning, maintenance and/or replacement.

It is to be understood that while the invention has been described above in conjunction with preferred specific embodiments, the description and examples are intended to illustrate and not limit the scope of the invention, which is defined by the scope of the appended claims.

We claim:

1. An ion source device for producing ionized molecules from a sample, comprising an ionization chamber having a top portion, a bottom portion and a back portion, wherein said chamber is formed from the combination of a chamber body and a corresponding chamber seal, and further wherein:

(a) the chamber seal defines the top portion and the back portion of the ionization chamber, said seal having a sample introduction means comprising a first passageway with a downstream terminus and traveling along a central axis thereof, wherein the sample introduction means passes through the top portion of the chamber and is capable of accepting a sample from a source and discharging the sample from the downstream terminus of the first passageway into the ionization chamber, said seal also having a shoulder for coupling to the chamber body; and (b) the chamber body defines the bottom portion and an exit interface portion of the ionization chamber, said body having a second passageway with a central axis that is arranged in transverse relation to the central axis of the sample introduction means, wherein the second passageway passes through the exit interface portion of the chamber and is capable of accepting sample molecules from the chamber, wherein the shoulder of the chamber seal and the exit interface portion of the chamber body are identically angled relative to a vertical axis.

2. The device of claim 1 wherein the chamber body further comprises an outlet means passing through the bottom portion of the ionization chamber.

3. The device of claim 2 wherein the outlet means is arranged in the chamber body such that it is in opposing relation to the downstream terminus of the first passageway when the chamber is assembled.

4. The device of claim 3 wherein the second passageway is contained within an electrically conductive housing having an opening arranged adjacent to the downstream terminus of the first passageway.

5. The device of claim 4 wherein the electrically conductive housing is connected to a first voltage source and the second passageway is connected to a second voltage source.

6. The device of claim 5 wherein the sample introduction means discharges the sample from the first passageway in the form of an electrospray containing charged molecules.

7. The device of claim 6 wherein charged molecules in the electrospray discharged from the first passageway are caused to move laterally through the opening in the housing and pass into the second passageway due to electrostatic attraction forces generated by the first and second voltage sources.

8. The device of claim 7 wherein the outlet means is arranged substantially opposite the downstream terminus of the first passageway in the ionization chamber, whereby excess electrospray can be rapidly removed from the chamber through said outlet means.

9. The device of claim 7 further comprising a third voltage source arranged adjacent to the downstream terminus of the first passageway.

10. The device of claim 9 wherein the third voltage source has an annular configuration and is arranged within the ionization chamber such that the electrospray discharged from the sample introduction means is substantially encircled by the third voltage source.

11. The device of claim 7 wherein the second passageway comprises a downstream terminus in fluid communication with an analytical apparatus, whereby charged molecules from the ionization chamber that have passed into the second passageway can be communicated to the analytical apparatus.

12. The device of claim 11 wherein the analytical apparatus is capable of detecting and measuring the mass-to-charge ratio and/or the mass and charge of the molecules that have been communicated from the downstream terminus of the second passageway.

13. The device of claim 12 wherein the analytical apparatus comprises a mass spectrometer.

14. The device of claim 1 wherein the sample introduction means is configured to accept nebulized sample molecules and discharge vaporized sample molecules from the downstream terminus of the first passageway.

15. The device of claim 14 wherein the chamber seal comprises a point charge voltage source on the back portion of the ionization chamber and arranged such that it is substantially adjacent to the downstream terminus of the first passageway, whereby said point charge voltage source forms a charged vapor containing charged molecules from the vaporized sample molecules discharged from the first passageway.

16. The device of claim 15 wherein the electrically conductive housing is connected to a second voltage source and the second passageway is connected to a third voltage source.

17. The device of claim 16 wherein charged molecules in the charged vapor are caused to move laterally through the opening in the housing and pass into the second passageway due to electrostatic attraction forces generated by the second and third voltage sources.

18. The device of claim 17 wherein the chamber body further comprises an outlet means passing through the bottom portion of the ionization chamber.

19. The device of claim 18 wherein the outlet means is arranged substantially opposite the downstream terminus of the first passageway in the ionization chamber, whereby excess vapor can be rapidly removed from the chamber through said outlet means.

20. The device of claim 17 wherein the second passageway comprises a downstream terminus in fluid communication with an analytical apparatus, whereby charged molecules from the charged vapor that have passed into the second passageway can be communicated to the analytical apparatus.

21. The device of claim 20 wherein the analytical apparatus is capable of detecting and measuring the mass-to-charge ratio and/or the mass and charge of the molecules that have been communicated from the downstream terminus of the second passageway.

22. The device of claim 21 wherein the analytical apparatus comprises a mass spectrometer.

23. A mass spectrometer which includes an ion source for producing ionized molecules from a sample, comprising a ionization chamber having a top portion, a bottom portion and a back portion, wherein said chamber is formed from the combination of a chamber body and a corresponding chamber seal, and further wherein:

(a) the chamber seal defines the top portion and the back portion of the ionization chamber, said seal having a sample introduction means comprising a first passageway with a downstream terminus and traveling along a central axis thereof, wherein the sample introduction means passes through the top portion of the chamber and is capable of accepting a sample from a source and discharging the sample from the downstream terminus of the first passageway into the ionization chamber, said seal also having a shoulder for coupling to the chamber body; and (b) the chamber body defines the bottom portion and an exit interface portion of the ionization chamber, said body having a second passageway with a central axis that is arranged in transverse relation to the central axis of the sample introduction means, wherein the second passageway passes through the exit interface portion of the chamber and is capable of accepting sample molecules from the chamber, wherein the shoulder of the chamber seal and the exit interface portion of the chamber body are identically angled relative to a vertical axis.

24. The mass spectrometer of claim 23 wherein the chamber body further comprises an outlet means passing through the bottom portion of the ionization chamber.

25. A liquid chromatography/mass spectrometry apparatus comprising:

(a) a liquid chromatography separation system for providing an effluent from a liquid sample;

(b) a liquid chromatography/mass spectrometry interface in fluid communication with the liquid chromatography system, comprising an ionization chamber formed from the combination of an angled chamber body and an angled chamber seal that are identically angled relative to a vertical axis, wherein the ionization chamber is capable of accepting effluent from the liquid chromatography system and producing an aerosol therefrom containing ionized sample molecules; and (c) a mass spectrometer in fluid communication with the liquid chromatography/mass spectrometry interface, said spectrometer capable of accepting ionized sample molecules from the interface and providing a mass spectrum of said sample.

26. The apparatus of claim 25 wherein the ionization chamber comprises a top portion, a bottom portion and a back portion, and further wherein:

(a) the angled chamber seal defines the top portion and the back portion of the ionization chamber, said seal having a sample introduction means comprising a first passageway with a downstream terminus and traveling along a central axis thereof, wherein the sample introduction means passes through the top portion of the chamber and is capable of accepting effluent from the liquid chromatography system and discharging said effluent from the downstream terminus of the first passageway into the ionization chamber; and (b) the angled chamber body defines the bottom portion and a mass spectrometer interface portion of the ionization chamber, said body having a second passageway with a central axis that is arranged in transverse relation to the central axis of the sample introduction means, wherein the second passageway passes through the mass spectrometer interface portion of the chamber to communicate with the mass spectrometer and is capable of accepting charged sample molecules produced in the chamber and passing said molecules to the mass spectrometer.

* * * * *